United States Patent [19]

Williams

[11] Patent Number: 5,331,840
[45] Date of Patent: * Jul. 26, 1994

[54] DETECTION OF A GAS LEAKED INTO A LIQUID WHICH HAS BEEN SAMPLED FROM A PLURALITY OF SPACES

[75] Inventor: William J. Williams, Indianapolis, Ind.

[73] Assignee: Sentech Corporation, Indianpolis, Ind.

[ * ] Notice: The portion of the term of this patent subsequent to May 26, 2009 has been disclaimed.

[21] Appl. No.: 886,231

[22] Filed: May 21, 1992

Related U.S. Application Data

[63] Continuation of Ser. No. 477,309, Feb. 8, 1990, Pat. No. 5,115,666.

[51] Int. Cl.⁵ .................. G01N 1/10; G08B 23/00
[52] U.S. Cl. .................. 73/19.1; 73/863.33; 73/864.81; 73/863.01; 340/605; 340/632
[58] Field of Search .......... 73/19.01, 19.1, 31.07, 73/19.02, 19.12, 23.41, 23.35, 863, 863.01, 863.31, 864.31; 340/605, 632

[56] References Cited

U.S. PATENT DOCUMENTS

| | | | |
|---|---|---|---|
| 1,990,706 | 2/1936 | Midgley, Jr. | 436/3 |
| 2,549,388 | 4/1951 | Rivers | 73/28.04 |
| 2,591,485 | 4/1952 | White | 324/468 |
| 2,902,414 | 9/1959 | Schmerzler | 203/10 |
| 2,987,912 | 6/1961 | Jacobson | 73/19.1 |
| 3,037,374 | 6/1962 | Messinger | 73/61.43 |
| 3,069,898 | 12/1962 | Vesper | 73/23.42 |
| 3,150,516 | 9/1964 | Linnenbom et al. | 73/19.1 |
| 3,209,343 | 9/1965 | Dunham et al. | 340/515 |
| 3,232,712 | 2/1966 | Stearns | 422/96 |
| 3,298,227 | 1/1967 | Hicks | 73/863.33 |
| 3,369,405 | 2/1968 | Galegar | 73/863.33 |
| 3,418,841 | 12/1968 | Issenmann | 73/19.01 |
| 3,455,144 | 7/1969 | Bradley | 73/19.1 |
| 3,472,632 | 10/1969 | Hervert | 422/242 |
| 3,522,151 | 7/1970 | Dismore | 202/236 |
| 3,535,088 | 6/1970 | Zimmeramn | |
| 3,565,767 | 2/1971 | Light | 203/11 |
| 3,572,085 | 3/1971 | Packo | 73/40.5 R |
| 3,590,247 | 6/1971 | Holford | 436/57 |
| 3,699,802 | 10/1972 | Hotta et al. | 73/863.31 |
| 3,716,334 | 2/1973 | Pont | 436/123 |
| 3,759,086 | 9/1973 | McAuliffe | 73/19.1 |
| 3,790,345 | 2/1974 | Mansfield et al. | 436/3 |
| 3,827,302 | 8/1974 | Sato | 73/863.33 |
| 3,846,075 | 11/1974 | Cioffi | 73/863.33 |
| 4,090,392 | 5/1978 | Smith et al. | 73/863.33 |
| 4,090,554 | 5/1978 | Dickinson | 165/1 |
| 4,129,418 | 12/1978 | Davis | 422/98 |
| 4,154,086 | 5/1979 | Button et al. | 73/19.1 |
| 4,192,175 | 3/1980 | Godai et al. | 73/19.07 |
| 4,198,208 | 4/1980 | Lerner et al. | 436/159 |
| 4,200,497 | 4/1980 | Rhodes | 202/197 |
| 4,225,314 | 9/1980 | Macourt | 436/26 |
| 4,304,752 | 12/1981 | Jenkins et al. | 422/98 |
| 4,317,995 | 3/1982 | Bradshaw et al. | 250/288 |
| 4,414,858 | 11/1983 | Peterson et al. | 73/863.33 |
| 4,472,354 | 9/1984 | Possell et al. | 73/23.41 |
| 4,550,011 | 10/1985 | McCollum | 422/82.03 |
| 4,565,086 | 1/1986 | Orr, Jr. | 73/19.09 |
| 4,618,855 | 10/1986 | Hardin et al. | 340/605 |
| 4,758,408 | 7/1988 | Krawetz et al. | 422/92 |
| 4,993,271 | 2/1991 | Varguson | 83/863.33 |
| 5,115,666 | 5/1991 | Williams | 73/19.1 |

Primary Examiner—Hezron E. Williams
Assistant Examiner—Michael J. Brock
Attorney, Agent, or Firm—Welsh & Katz, Ltd.

[57] ABSTRACT

A method for discovering amounts of halogen in a liquid is provided wherein the a reservoir comprising the liquid and suspected halogen is healed to a temperature characteristic of the solubility of halogen in the liquid to provide a vapor. After condensing, a sampling vapor is provided to from which the amount of halogen may be detected.

9 Claims, 3 Drawing Sheets

DETECTION OF A GAS LEAKED INTO A LIQUID WHICH HAS BEEN SAMPLED FROM A PLURALITY OF SPACES

This is a continuation of copending application Ser. No. 07/477,309 filed on Feb. 8, 1990, U.S. Pat. No. 5,115,666.

FIELD OF THE INVENTION

The present invention relates to detection apparatus and methods. In particular, the invention relates to apparatus and methods for detecting the presence of halogen gases dissolved in a liquid such as water.

BACKGROUND OF THE INVENTION

In industrial systems, and particularly, in refrigeration systems, the mixture of water with liquid refrigerants is undesirable. For example, the presence of excess water in liquid refrigerants may freeze at low temperatures and restrict or completely prevent the flow of expansion valves, capillary tubings, and the like.

In addition, the solubility of amounts of refrigerant in liquids such as water is of considerable concern in refrigeration systems such as drinking water coolers, water cooled condensers and the like where small amounts of the refrigerant are introduced with water or other liquids either through equipment failure, or in some instance, by faulty design. The presence of excess water in halogen may cause corrosion in the system. In particular, such water may cause the hydrolysis of leaky halogenated refrigerant with the formation of acids. These acids tend to corrode metals as well as insulation and nonmetallic parts of the system. This condition is especially problematic during charging of the refrigeration system. Accordingly, detection of the halogen contaminant is essential to the operation and maintenance of these systems.

In a typical refrigeration system, there are at least first and second loops. The first is a closed loop for circulating a refrigerant, typically a well known halogen refrigerant. The first, refrigerant loop includes a motor-driven compressor for compressing the inputted halogen, thus converting the halogen refrigerant from a gaseous to a liquid state and outputting a heated halogen liquid. The heated halogen liquid is supplied to a condenser, which cools the halogen liquid. Typically, such condensers include a serpentine shaped tube, typically made of copper, for receiving and circulating the warm liquid halogen, and a shell for enclosing the serpentine shaped tube and circulating water thereabout, whereby the liquid halogen is cooled. The cooled liquid halogen is next directed through an expansion valve and into an evaporator. The valve causes the liquid halogen to expand and to change from a liquid to a gaseous state within the evaporator. As the halogen changes from a gaseous to a liquid state, it absorbs heat thereby providing significant cooling. The cooled halogen gas is returned through the first loop from the evaporator to the compressor, whereby this cycle continues.

A trouble point in such refrigeration systems occurs in the condenser when the water circulating over the copper tubing wears by friction between the water and the tubing holes in the tubing, thereby causing a mixture of the halogen and water. Most (but not all) refrigerants are circulated in the first, refrigeration loop under positive pressure so that when a leak occurs in the condenser tubing, halogen will flow into the cooling water and dissolve the water therein. The second loop in which the cooling water flows varies from refrigeration system to refrigeration system. In some systems, the cooling water may be drawn from a river and after cooling returned to the river. In other systems, the cooling water may be passed to a cooling tower and allowed to fall down over a series of baffles. Typically, such water towers are open to the atmosphere, whereby if there has been a halogen leak, the solution of water and halogen is exposed to the atmosphere and halogen will be released into the atmosphere with possible damage to the environment and in particular to the ozone layer.

In those refrigeration system where the refrigerant is maintained under a negative pressure, water will be drawn through the holes into the first, refrigerant loop. Thereafter, the solution of water and halogen is returned from the evaporator to the condenser. Significant cooling of that solution takes place in the evaporator, whereby the water is converted to ice. When that ice is introduced into the compressor, the ice may readily damage the compressor and its motor, thereby bringing the operation of that refrigeration system to a halt.

Alternatively, there are refrigerant systems which incorporate an evaporator acting as a heat exchange device, whereby the expanding halogen gas passes through the evaporator in the form of a serpentine shaped coil surrounded by a shell for receiving a liquid, typically water, to be cooled. The water circulating over the evaporator tube may cause holes to wear therein, whereby a mixing of the halogen and water occurs. In such an embodiment, the cooled water is typically circulated through a second closed loop to cool an environment and thereafter return to be recooled by the evaporator. As described above, the presence of water and halogen is particularly corrosive. In those instances where the refrigerant is positively pressurized, halogen will be forced through the tube holes into the second closed cooling loop, thus contaminating the circulated water. Eventually, there is a strong possibility that the second loop will be corroded to the extent that holes will develop therein, whereby the water contaminated with halogen will leak directly into the surrounding environment. Again, possible contamination of the environment is likely.

In either of the above described refrigeration systems, wearing and contamination may occur with the result that water may become contaminated with the halogen. Therefore, it is important to be able to detect the presence of water dissolved in halogen so that contaminated refrigeration systems may be shut down and detected leaks of halogen repaired.

Prior art approaches to similar problems of this nature require heating the sample water having suspected contamination to temperatures by which the water may be expanded and thereby introduced to sensing apparatus. U.S. Pat. No. 4,154,086 to Button et al describes such an approach for the detection of volatile organic compounds such as hydrocarbons in water solutions used in petrochemical systems. A carrier gas such as nitrogen is introduced into the water solution containing the hydrocarbons. The water solution is thereafter heated to elevated temperatures in excess of 150° F., whereby a water vapor solution containing the carrier gas and hydrocarbons is formed. After a condensing step, the remaining hydrocarbons are applied to a detector.

Generally, however, the solubility of halogenated refrigerants in water is an important consideration in the detection of the amount of halogen present. At extreme temperatures, the solubility of halogen in water and other liquids increases and it becomes increasingly difficult to condense the vapor solution to separate the halogen from the water for accurate detection. Accordingly, while prior art approaches may provide satisfactory solutions for their intended uses, they are incapable of dealing with the problem of detection of amounts of a halogen in a liquid.

OBJECTS OF THE INVENTION

It is therefore a general object of the present invention to provide an improved method for detecting halogenated gases in a liquid.

It is an additional object of the present invention to accurately detect trace amounts of halogen gases in a liquid.

A further object of the invention is to minimize the solubility of a liquid in a halogen gas for increased accuracy in the detection of subsequently released halogen.

An additional object of the present invention to provide a method for detecting halogenated gases in a liquid for continuous monitoring of such gases.

A still further object of the present invention is to provide a method for detection which is capable of more accurate and quantitative measurement than is heretofore known.

Other objects and advantages of the invention will become apparent upon reading the following description and appended claims, and upon reference to the accompanying drawings.

SUMMARY OF THE INVENTION

These objects are achieved with a method of discovering amounts of halogen in a solution of halogen and a liquid that uses a minimized evaporation temperature of the solution to reduce the solubility of the liquid in halogen. The method according to the present invention accomplished this by providing a sample of the liquid in a reservoir. The reservoir is heated to an evaporation temperature attributable to the solubility of the liquid in halogen to provide a vapor solution of halogen and liquid. The vapor solution is thereafter condensed to remove a portion of the liquid and provide a sampling vapor. In this way, an amount of halogen may be detected in the sampling vapor.

BRIEF DESCRIPTION OF THE DRAWINGS

For a more complete understanding of this invention, reference should now be made to the embodiment illustrated in greater detail in the accompanying drawings and described below by way of example of the invention.

DETAILED DESCRIPTION OF THE PREFERRED EMBODIMENT

The following detailed description will permit a more complete understanding of this invention. However, the embodiment described below is simply an example of the invention, and the invention will not be limited to this embodiment. It will be understood that the methods and apparatus of the invention may be implemented with the use of various configurations with appropriate modification. It will be further understood, that in certain instances, details may have been omitted which are not necessary for an understanding of the present invention.

Generally, the present invention relates to a method for detecting the presence of halogen in a solution of halogen and a liquid. The present invention uses information related to the solubility of the liquid dissolved in halogen for setting an appropriate evaporating temperature of the solution. By so doing, the amount of the evaporated liquid is controlled. In addition, the halogen detecting means used by the present invention may detect small amounts of halogen with increased accuracy. The apparatus and method according to the preferred embodiment samples a liquid solution comprising water. It will be understood by those skilled in the art to which this invention pertains, that other liquids such as brine or glycol may be sampled just as easily with slight modification.

Figure 1:
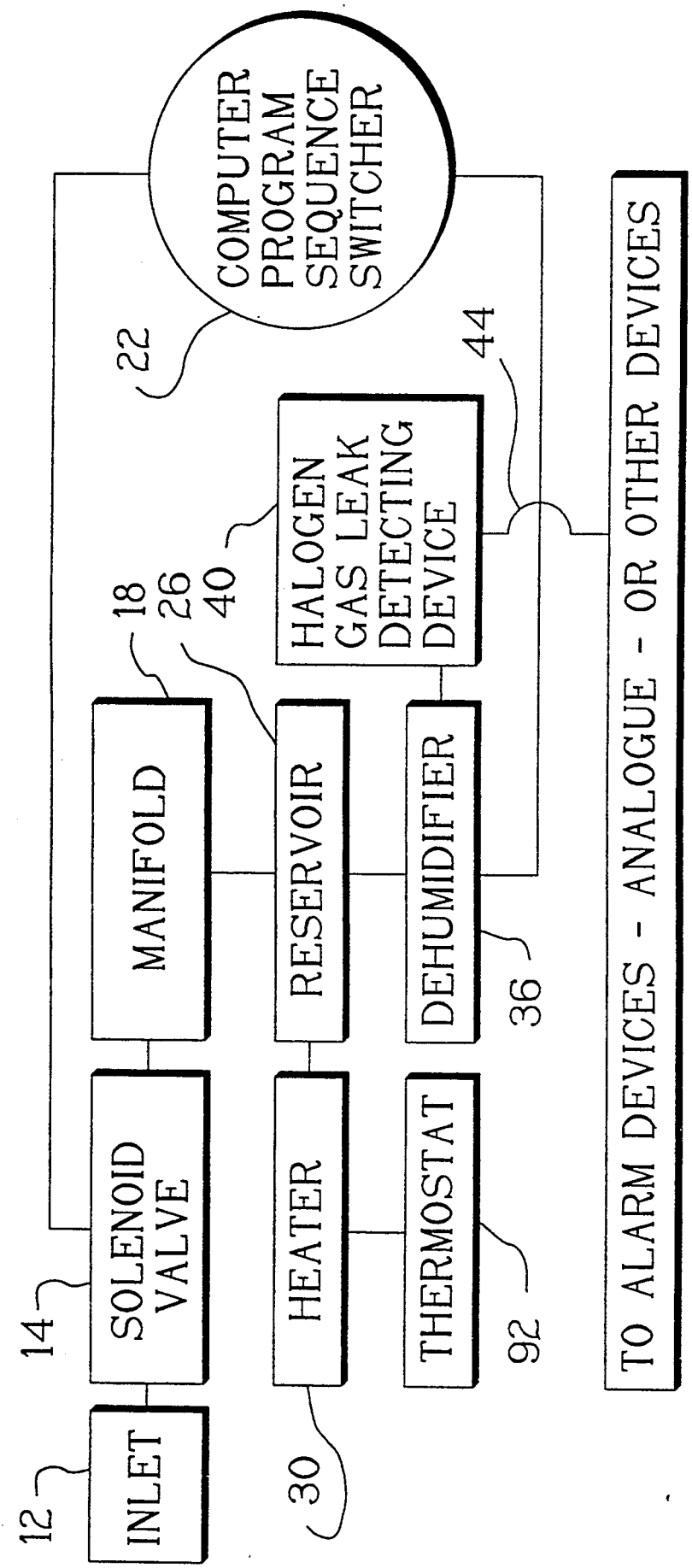
FIG. 1 is a block diagram representation of a halogen leak detection apparatus in accordance with the present invention.

Turning now to the drawings, FIG. 1 shows a block diagram representation of a halogen detecting apparatus 10 according to the present invention. A liquid such as water having a suspected amount of halogen gas to be detected is directed from a source (not shown) into a fluid inlet 12. In an illustrative application, the inlet 12 may be coupled to receive water from the discharge side of a condenser disposed in the first, refrigerant loop of the refrigeration system as described above. An actuable valve 14, in communication with the fluid inlet 12 directs the liquid through a fluid manifold 18. A controller 22 provides appropriate control signals to actuate or deactuate the valve 14 to control the amount of liquid provided to the fluid manifold 18. Upon receiving the liquid, the fluid manifold 18 provides a passageway to a fluid reservoir 26.

A heating element 30 associated with the fluid reservoir 26 controls the temperature of the liquid solution dependent upon the solubility of the liquid in that gas. The heating element 30 heats the solution to a minimum temperature to release a vapor solution of water and halogen. The vapor solution is directed to a dehumidifier 36 for removing remaining water from the vapor solution and thereafter, to provide a sampling vapor for detection. The dehumidifier 36 also receives control signals provided by the controller 22.

A halogen gas detecting device 40 detects the amount of halogen derived from the dehumidifier 36 and thereafter provides an output signal on a line 44 indicative of the amount of halogen detected.

Figure 2:
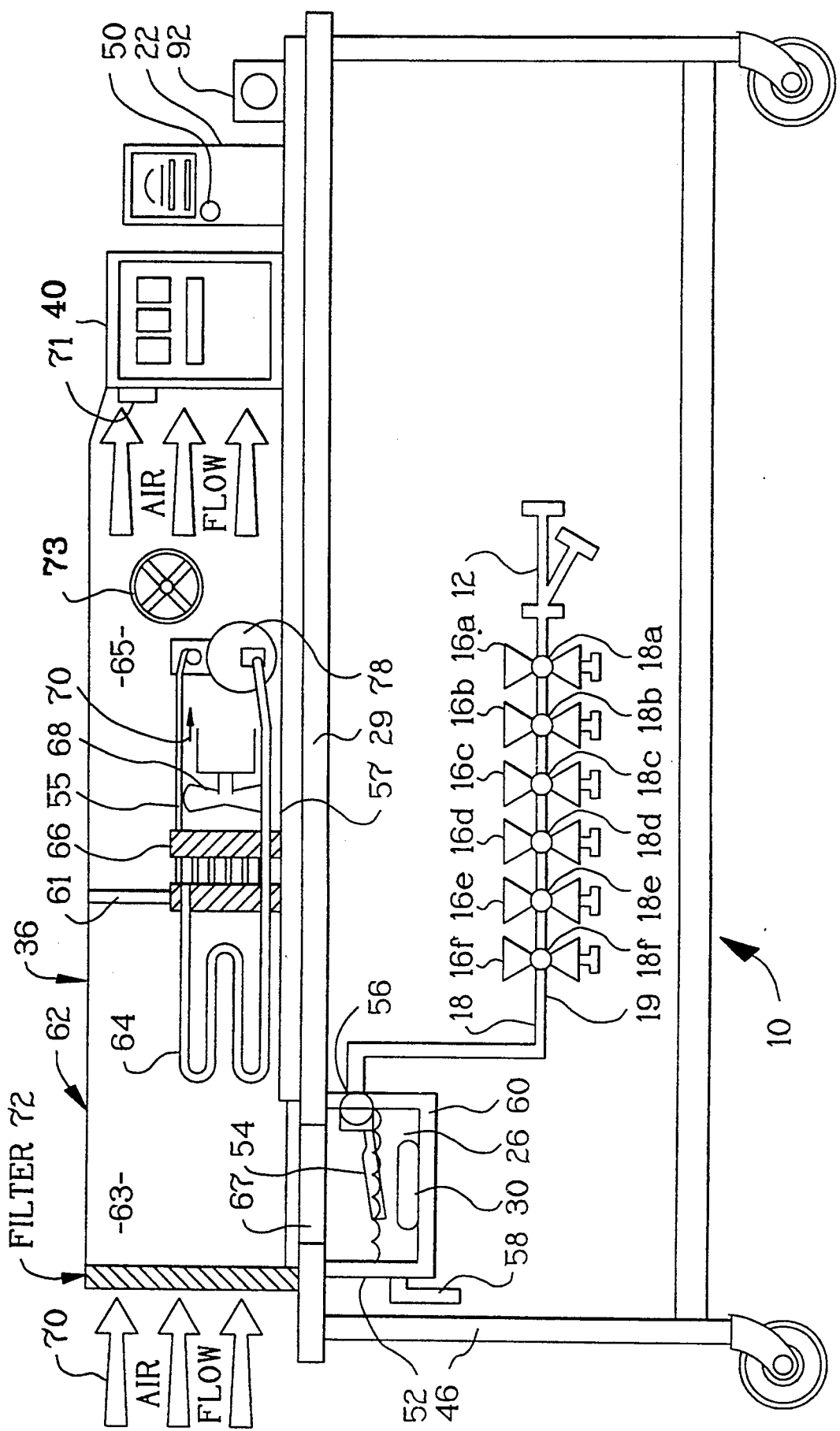
FIG. 2 is a schematic representation of the halogen leak detection apparatus of FIG. 1 showing its components in one arrangement of the present invention.

Turning now to FIG. 2, therein is shown a schematic representation of the detecting apparatus 10 of the present invention. As shown in FIG. 2, the detecting apparatus 10 may be conveniently placed on a movable industrial cart 46 or other suitable means for easy portability.

A source of liquid is received from a water cooled condenser, chiller barrel, or other industrial refrigerant vessel (not shown) having a suspected presence of a halogenated gas. Refrigerants stored in such cylinders, receivers, condensers and the like achieve an equilibrium between a liquid and gaseous state. With most halogenated refrigerants, the concentration of water in the gaseous portion is greater than in the liquid phase. Accordingly, the refrigerant becomes wetter as the vapor is removed.

With certain refrigerants, however, the situation is reversed. The ratio of concentration of water between the vapor and liquid is higher at low temperatures than at higher temperatures. This distribution of water results in a drier remaining liquid when the vapor is removed from the container. Since a higher concentration of water is removed with the removal of the vapor, a refrigerant changed in this way will have a higher concentration than that originally in the container.

The liquid having a suspected presence of halogenated refrigerant enters the fluid inlet 12 in communication with a plurality of actuable valves 16a through 16f. Preferably, the valves 16a through 16f are solenoid valves suited for most types of industrial applications and used for water, light oils, air lines and the like. With the use of a plurality of valves, multiple sources of sampling liquid may be introduced to the detection apparatus 10. Of course, the present invention could work just as easily with one valve receiving liquid from a singular source. A stainless steel insert (not shown) may be used for protection when the liquid source contains glycol type solutions which tend to otherwise corrode the actuable valves 16a through 16f. For example, one valve 16a could control the input of water from the discharge side of the condenser and a second valve 16b could control the input of liquid from the discharge of the evaporator of that refrigeration system described above.

In the preferred embodiment, the valves 16a through 16f are mounted to the manifold 18 comprising a single manifold body 19 having multiple receiving ports 18a through 18f formed to receive the valves 16a through 16f, respectively. In this way, the output of the valves 16a though 16f is directed into the manifold 18.

A programmable controller or sequencer 22 provides control signals to the valves 16a through 16f to actuate a desired valve and to control the amount of liquid introduced to the detecting apparatus 10. In the preferred embodiment, the programmable controller 22 is an SLC 100 processor unit manufactured by Allen-Bradley, having a central processing unit, RAM memory, a power supply, and battery backup power supply as will be understood by those skilled in the art.

A timer counter access terminal may be used in conjunction with the controller 22 to access programmed timer, counter and sequencer data. This feature advantageously allows production, supervisory, and maintenance personnel to monitor data generated by the detecting apparatus on a real-time basis. Preferably, I/O addresses may also be accessed such that appropriate software modification may be provided to the controller 22 to accommodate varied processes or part changes. In addition, a key switch 50 may be provided to gain access to functions of the controller 22, thereby preventing unauthorized modification.

From receipt of control signals provided by the controller 22, the valves 16a through 16f direct the fluid through the manifold 18 into a sampling reservoir 26. The reservoir is contained in a sampling tank 52, preferably fabricated of stainless steel of 0.08 gauge having dimensions of a height of approximately nine inches and a base 60 dimensioned five inches wide by ten inches long.

A float assembly 54 including a float valve 56 is positioned within the sampling tank 52 to prevent the liquid reservoir 26 from overflowing. When the amount of liquid exceeds a threshold level as determined by the float valve assembly 54, the float valve 56 closes to prevent excess liquid from entering the liquid reservoir 26. A Robert Valve Action Float Assembly manufactured by Robert Valves is preferred.

The liquid reservoir 26 within the sampling tank 52 maintains a flow rate of approximately one half gallons per minute. The liquid exits the sampling tank via an open drain 58.

A submersible heater 30 is mounted to the base 60 of the sampling tank 52, and is preferably controlled with the use of a thermostat 92. The thermostat 92 maintains the liquid reservoir 26 at a selected temperature illustratively not less than 70° F. As will be explained, the selected temperature is carefully set to ensure that trace amounts of the halogen may be accurately detected, dependent upon the solubility of the liquid, typically water, in the refrigerant, illustratively a halogen.

A table detailing the solubility in water of commercially available halogen refrigerants, which are denoted as "R-13" as will be understood by those skilled in the art, is shown in the Table below:

TABLE

| SOLUBILITY OF WATER IN LIQUID REFRIGERANTS | | | | | | |
|---|---|---|---|---|---|---|
| | Solubility in Parts per Million by Weight | | | | | |
| Temp., °F. | R-11 | R-12 | R-22 | R-113 | R-114 | R-502 |
| 100 | 168 | 165 | 1800 | 168 | 148 | 740 |
| 80 | 113 | 98 | 1350 | 113 | 95 | 560 |
| 60 | 70 | 58 | 970 | 70 | 57 | 440 |
| 40 | 44 | 32 | 690 | 44 | 33 | 300 |
| 20 | 26 | 17 | 470 | 26 | 18 | 185 |
| 0 | 15 | 8 | 308 | 15 | 10 | 120 |
| −20 | 8 | 4 | 195 | 8 | 5 | 70 |
| −40 | 4 | 2 | 120 | 4 | 2 | 40 |
| −60 | 2 | 1 | 68 | 2 | 1 | 20 |
| −80 | >1 | >1 | 37 | >1 | >1 | 12 |

From the above Table, it is seen that if the values of solubility of water in these halogen refrigerants in parts per million (ppm) were plotted as a function of temperature, that each of the listed halogen refrigerants would have a curve comprising a first portion sloping upward at a first rate to a certain point or knee, and a second portion continuing upward from the knee at a second rate greater than the first. By observation of the above chart, it can be seen that the knee of the curves generally falls between 70° and 100° F. The selected temperature at which the water within the reservoir is heated is determined based upon the solubility of water in halogen and is typically set in the range of 70° and 100° F. and optimally at 75°. If the evaporation temperature is increased beyond this range, it can be seen that the ppm of water will significantly increase as a function of temperature. Thus at such elevated temperatures, the released vapor solution of water and halogen contains a relatively high percentage of water vapor, which will potentially interfere with the subsequent measurement of halogen by the detector 40. On the other hand, if the temperature is decreased below this range, significantly lower amounts of halogen are released and the measurements of such minimal amounts may be inaccurate. Thus, the process of sensing the halogen is optimized by setting the selected evaporation temperature of the solution within the reservoir 30 at an optimum temperature at or just below the knee of the curve of the solubility of water in the refrigerant as a function of temperature.

Inasmuch as the liquid reservoir 26 is a typical volume liquid within an open container (sampling tank 52), it has been found that temperatures above 70° F. provide better escaping moisture vapors. It has been found that for solutions of halogen and water, the evaporation temperature should not be greater than 100° F., and preferably does not exceed 75° F. As the temperature is increased, the halogens to be detected become more soluble in water and it becomes increasingly difficult to condense the vapor solution to separate the halogen from the water in a subsequent condensing step. The arrangement in the present invention advantageously minimizes the solubility of the halogen in the water, whereby most of the water vapor may be condensed leaving relatively pure halogen gases to be detected during subsequent condensing of the vapor solution.

As particularly shown in FIG. 2, the detecting apparatus 10 is placed upon the industrial cart 46, which includes a horizontally disposed table surface 29. The tank 52 for containing the sampling reservoir 26 is mounted below the surface 29 and in communication with an opening 67 therethrough. An enclosure 62 is mounted on top, as shown in FIG. 2, and includes a centrally disposed partition 61 dividing the enclosure 62 into a first chamber 63 and a second chamber 65. The first chamber 63 is aligned with the opening 67 to receive the vapors expelled from the sampling reservoir 26. These vapors are drawn from the chamber 63 to the dehumidifier 36, such as an EBAC Industrial Humidifier Model No. CD-30. As is typical within such a dehumidifying device, an evaporator coil 64 is mounted adjacent a condenser 66. The evaporator coil 64 evaporates approximately 50% of the water present within the sampling vapor provided by the liquid reservoir 26. An additional 5 to 10% of the water within the vapor is eliminated by heat generated by the condenser 66. The dehumidifier 62, as illustratively identified above, comprises a compressor 78 for circulating a refrigerant through an output line 57 to the condenser 66, wherein the refrigerant expands within the evaporative coil 64 to cool the vapor introduced into the first chamber 63, to a temperature illustratively set at 37° or 38°. At such a temperature, the condenser coil 64 removes approximately 50% of the water vapor from the solution vapor. Thereafter, the refrigerant returns to the condenser 66, wherein the refrigerant is heated to a temperature in the order of 110° F. The vapor is drawn by the fan 68 over the condenser 66, whereby the vapor is subjected to a further, second step of dehumidification, whereby approximately 5% to 10% of the water vapor is further removed. The refrigerant is returned through a line 55 to the compressor 78, whereby this cycle continues.

The vapor is drawn into the condenser 66 with the use of condenser fan 68 in the direction denoted by the arrow 70. As will be appreciated by those skilled in the art to which this invention pertains, an air filter 72 is placed at an entrance to the enclosure 62. The fan 68 is capable of drawing the ambient atmosphere through the filter 72 into the first chamber 63, whereby the presence of halogen in the ambient atmosphere, as well as the vapor expelled from the reservoir 26, may be detected. The velocity of the ambient atmosphere (air) flow passing over the reservoir sampling tank 52 is, in the preferred embodiment, approximately 50 feet per minute.

The halogen gas molecules in the vapor are quite stable. Accordingly, these molecules do not condense in the dehumidification process. The sampling air expelled from the condenser 66 maintain approximately 40–50% relative humidity, i.e., approximately 40–50% of the water within the vapor does not condense. As a result, a sampling vapor containing any halogen gases that may be present is provided.

The evaporation rate per ASHRAE is 3.5 pints per day, and may be represented by the following equation:

$$W = \frac{A(95 + 0.425v)(Pw - Pa)}{Y}$$

where:
W = 1 lb./hour evaporated
A = surface area (2 square feet)
v = velocity on surface (50 feet/sec.)
Y = latent heat of vapor (1045 BTU/10)
Pw = Vapor pressure $H_2O$ (1.213 inches Hg)
Pa = Vapor pressure ambient (0.522 inches Hg)

A relative humidity transmitter 73 is positioned downstream of the dehumidifier 36. The transmitter 73 continuously monitors and displays the relative humidity of the sampling air. In the preferred embodiment, the transmitter 73 is preset with a threshold of 80% relative humidity. If the relative humidity exceeds 80%, the transmitter 73 provides a disable signal to the controller 22. If the relative humidity should exceed 80%, there is a strong likelihood that the gas detector 40 may malfunction. The detector 40 of a preferred embodiment is fully described in copending U.S. Ser. No. 134,293, now U.S. Pat. No. 4,910,463, incorporated herein by reference. The detector 40 described therein employs a sensor which detects halogen based upon an increased ionization in the presence of halogen. In particular, halogen is passed between anode and cathode elements of the sensor. Halogen is detected by an increase in the ionization current drawn from the cathode element. If such a halogen sensor were employed, a vapor having a relatively high humidity in excess of 80% may well cause the sensor to malfunction and, in particular, to cause a discharge between the cathode and anode elements. Such a discharge, due to the presence of a relatively low conductive path between the sensor elements, will give an erroneous reading and may well cause damage to the sensor itself. As disclosed in the noted application, the detector 40 upon detecting halogen above predetermined levels will automatically disconnect power from its sensor to avoid damage thereto. Upon receipt of such information, the controller 22 may provide appropriate signals to sound an alarm or for other devices to indicate that the dehumidifier 36 has malfunctioned. The noted disabling signal provided by the detector 40 may also be used as a control signal to turn off the fan 68. It will be appreciated that the relative humidity transmitter 73 may also have indication means such as an LED display for visual monitoring by operating personnel.

However, if the relative humidity of the sampling vapor is within the limits set by the relative humidity transmitter 73, the sampling vapor is directed to the halogen gas leak detector 40. As shown in FIG. 2, the enclosure 62 confines and directs the dehumidified vapor to an inlet 71 of the detector; in turn, the vapor is directed to a sensor (not shown), which operates as described in the above-identified application to sense the presence of halogen. The detector 40 analyses the sampling vapor in ppm and includes variable trip point settings which may be preselected. Accordingly, if a desired trip point setting is exceeded from the detection of the concentration of halogen gas in the sampling air, the detector 40 sends appropriate signals via analog, digital, or dry contact communication to indicate an undesired concentration of halogen gas.

Inasmuch as the detector 40 comprises a resident microprocessor, the detector 40 may concurrently provide signals to the actuating valves 16a through 16f. In this way, the actuating valves 16a through 16f may become deenergized, causing the valves 16a through 16f to close and preventing further liquid from entering the detecting apparatus. In this condition, the fluid reservoir 26 drains through the open drain 58. Appropriate signals may be concurrently applied to the dehumidifier 36 for deactivating the same.

Figure 3:
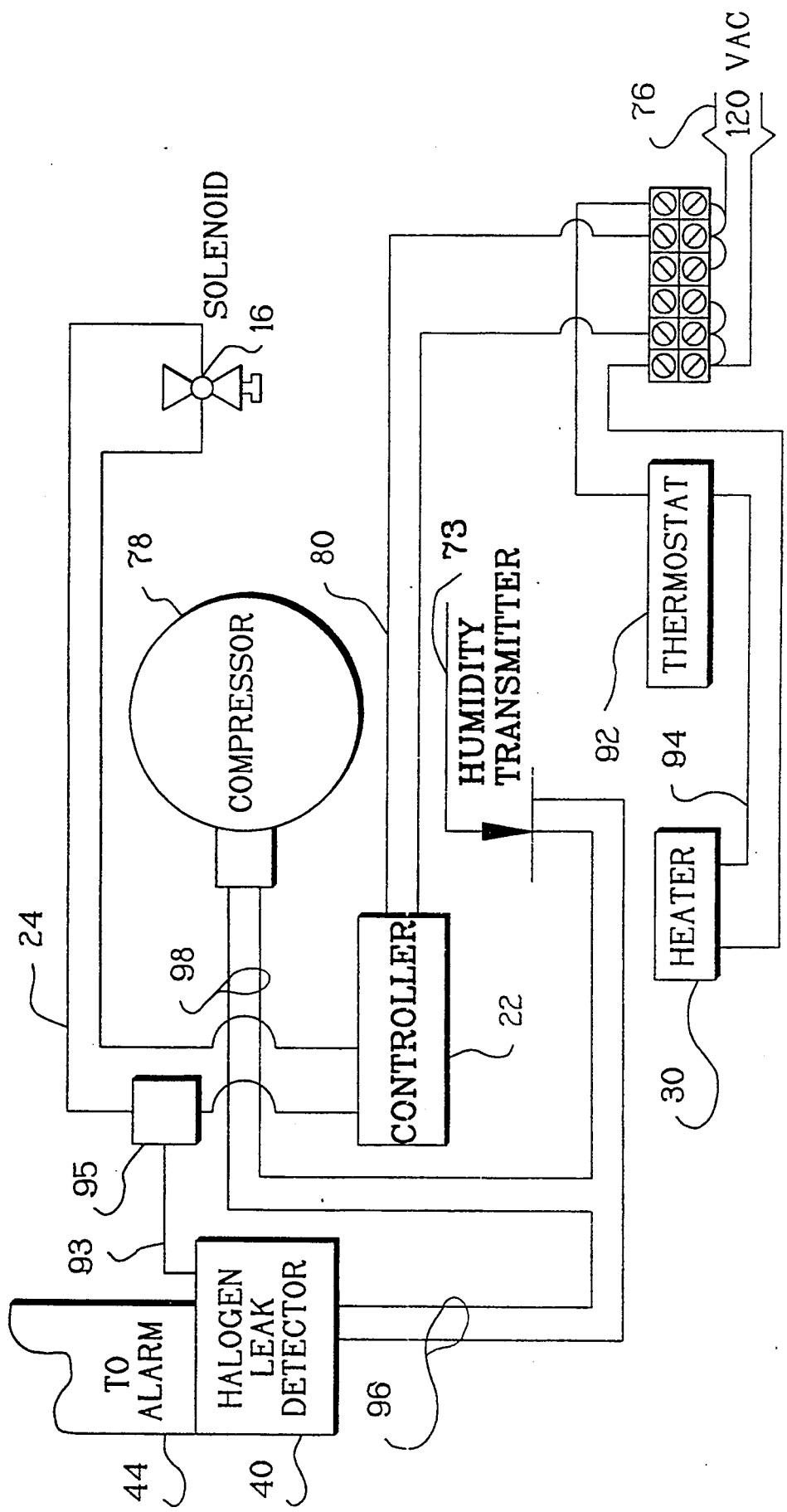
FIG. 3 is a diagrammatic representation of the electrical circuit elements in the leak detection apparatus of FIG. 1.

Turning now to FIG. 3, therein is shown a simplified electrical schematic diagram of the present invention. A conventional power source 76 supplies electrical power to the controller 22, the heater 30, the actuated valves 16a through 16f, a compressor 78 in the dehumidifier 36, and the halogen leak detector 40. The thermostat 92 controls the temperature of the heater 30 via the line 94. The humidity transmitter 73 upon sensing excess humidity applies signals to shutdown the halogen leak detector 40 and the dehumidifier 36 via the lines 96 and 98 respectively. In particular, the fan 68 is deactivated upon sensing excess humidity to prevent possible damage to the detector 40 and its sensor. The controller 22 provides central signals to the actuated valves 16a through 16f via the line 24. The halogen leak detector 40 provides signals to actuate an appropriate alarm (not shown) via the line 44. Further, the detector 40 applies a signal via line 93 to open a relay switch 95, whereby the circuit formed by the lines 24 to the solenoid valves 16 is opened and the valves 16 are closed. Thus, it is seen that when the halogen leak detector 40 senses a preset level of halogen dependent upon the refrigerant employed, the detector 40 will cause the solenoids 16 to close, thereby preventing further liquid to be brought to the sampling reservoir 26.

EPA standards have been established for each of the refrigerants. As described in the above noted application, threshold levels of halogen gas may be variously set to be detected, whereby this apparatus 10 may be used for various refrigerants. For example, the refrigerant R12 has a toxicity level of 1000 ppm, whereas the refrigerant R23 has a threshold level of 100 ppm.

In use, the cart 46 and the apparatus 10 may be moved to a selected location having an environment whose halogen level needs to be monitored. In one illustrative use, the apparatus may be conveniently disposed within the compressor room of a large refrigeration system as described above. At least one of the solenoid valves 16 may be connected to the discharge side of the condenser as disposed in the refrigerant loop of that system. If there has been a leak of the halogen from the refrigerant loop the water and halogen solution is directed via the selective valve 16 to the sampling reservoir 26, where it is heated and vapors are released and drawn through opening 27 into the dehumidifier 36. After a two-step process of water vapor removal, the relatively water free halogen vapor is directed to the gas detector 40.

In addition, the apparatus 10 of this invention is also capable of measuring the presence of halogen in the ambient atmosphere thereabout. In such an application, an airflow as indicated by the arrows 70 is drawn through the filter 72 into the first chamber 63. This airflow is directed by the condenser fan 68 to the detector 40, which is also capable of detecting halogen in that flow. Initially, when the detector 40 responds to a level of halogen above the set threshold, the operator does not know whether the indicated halogen leak is from the water drawn from the condenser or from the ambient atmosphere within the compressor motor room. After the first alarm, the operator (or it could be done automatically) shuts off the related valve 16 and the monitoring process continues. If the halogen detector 40 again indicates the presence of halogen above the threshold value, the second detection indicates that the halogen was present in the airflow. Conversely, if the detector 40 does not indicate again the presence of halogen after the solenoid valve 18 has been closed, there is an indication that the halogen leak was from the condenser.

A novel detecting apparatus and method meeting the aforestated objects has therefore been described. The invention detects the amount of halogen in a liquid by controlling the temperature of the solution in accordance with properties characteristic of the halogen gas to be detected bearing upon its solubility in that liquid. It will be understood by those skilled in the art to which this invention pertains that various modifications may be made in detail and arrangement of the processes and of the structures described herein in order to explain the nature of the invention without departing from the principles of the foregoing teachings. Accordingly, the invention will only be limited as expressed in the appended claims.

What is claimed is:

1. Apparatus for taking samples of a liquid from a plurality of corresponding spaces and monitoring the samples of liquid to detect a leak into the liquid of a given gas of a given concentration level which is greater than a residual level of the given gas, said apparatus comprising:
   a) a plurality of actuable valves, each of said valves in communication with a respective one of said plurality of spaces;
   b) a common sampling reservoir in communication with each of said plurality of valves for receiving the sample of the liquid from an actuated one of said plurality of valves;
   c) means for separating the given gas present in the liquid of the sample in said sampling reservoir;
   d) gas detecting means in communication with said sampling reservoir for detecting the presence of the separated gas of a concentration above the given concentration level to provide an alarm indicative of a valid leak of the given gas into a corresponding liquid sample; and
   e) controlling means including means coupled with each of said plurality of actuable valves for selectively actuating one of said plurality of valves to permit the introduction of one sample of the liquid at a time from the corresponding one of said plurality of spaces into said sampling reservoir and the subsequent detection by said gas detecting means of the separated given gas in the one sample.

2. The apparatus of claim 1, wherein said controlling means includes means for deactuating said one actuated valve in response to said alarm.

3. The apparatus of claim 1, wherein there is further included actuatable fan means disposed in communication with said sampling reservoir for conveying the separated given gas to said gas detecting means, and said controlling means is responsive to said alarm for deactuating said fan means.

4. The apparatus of claim 1, wherein there is further included drain means attached to a bottom portion of said sampling reservoir.

5. The apparatus in claim 1, wherein there is included means for limiting the volume of the sample of the liquid introduced into said sampling reservoir to a given level.

6. The apparatus in claim 5, wherein said limiting means comprises means for sensing the liquid level within said sampling reservoir above said given level to apply a deactivating signal to said controlling means, whereby said one activated valve is deactivated.

7. A method for taking samples of a liquid from a plurality of corresponding spaces and monitoring the samples for the suspected presence of a given gas leaked into the liquid in any of said plurality of spaces of a given concentration level greater than a residual level of the given gas, said method comprising the steps of:
   a) taking one sample of the liquid at a time from a selected one of the plurality of spaces and introducing the one liquid sample into a common sampling reservoir;
   b) separating the given gas present in the liquid of the one sample introduced into the sampling reservoir;
   c) conveying the given gas separated into the sampling reservoir to a sensor; and
   d) operating the sensor to detect the presence of the given gas separated from the one sample of a concentration above the concentration level to produce an alarm indicative of a valid leak of the given gas into a corresponding liquid sample.

8. The method of claim 7, wherein the sample introduced into the sampling reservoir is removed before the next sample from another space of the plurality is introduced thereto.

9. Apparatus for taking samples of a liquid from a plurality of corresponding spaces and monitoring the samples of liquid to detect a leak into the liquid of a given gas of a given concentration level which is greater than a residual level of the given gas, said apparatus comprising:
   a) a single conduit having a plurality of ports therein;
   b) a corresponding plurality of actuable valves, each of said valves in communication with a respective one of said plurality of spaces and a respective one of said plurality of ports;
   c) a common sampling reservoir coupled to said single conduit for receiving the sample of the liquid from an actuated one of said plurality of valves;
   c) means for separating the given gas present in the liquid of the sample in said sampling reservoir;
   d) gas detecting means in communication with said sampling reservoir for detecting the presence of the separated gas of a concentration above the given concentration level to provide an alarm indicative of a valid leak of the given gas into a corresponding liquid sample; and
   e) controlling means including means coupled with each of said plurality of actuable valves for selectively actuating one of said plurality of valves to permit the introduction of one sample of the liquid at a time from said corresponding one of said plurality of spaces into said sampling reservoir and the subsequent detection by said gas detecting means of the separated gas in the one sample.

* * * * *